US009708722B2

United States Patent
Teamey et al.

(10) Patent No.: US 9,708,722 B2
(45) Date of Patent: Jul. 18, 2017

(54) ELECTROCHEMICAL CO-PRODUCTION OF PRODUCTS WITH CARBON-BASED REACTANT FEED TO ANODE

(71) Applicant: Liquid Light, Inc., Monmouth Junction, NJ (US)

(72) Inventors: Kyle Teamey, Washington, DC (US); Jerry J. Kaczur, North Miami Beach, FL (US)

(73) Assignee: Avantium Knowledge Centre B.V., Amsterdam (NL)

( * ) Notice: Subject to any disclaimer, the term of this patent is extended or adjusted under 35 U.S.C. 154(b) by 386 days.

(21) Appl. No.: 14/463,430

(22) Filed: Aug. 19, 2014

(65) Prior Publication Data

US 2014/0357904 A1    Dec. 4, 2014

Related U.S. Application Data

(62) Division of application No. 13/724,647, filed on Dec. 21, 2012, now Pat. No. 8,845,876.
(Continued)

(51) Int. Cl.
C25B 3/00 (2006.01)
C25B 3/02 (2006.01)
(Continued)

(52) U.S. Cl.
CPC ............... *C25B 3/00* (2013.01); *C07C 1/26* (2013.01); *C07C 29/149* (2013.01); *C07C 29/58* (2013.01);
(Continued)

(58) Field of Classification Search
None
See application file for complete search history.

(56) References Cited

U.S. PATENT DOCUMENTS

| 1,280,622 A | 10/1918 | Andrews |
| 1,962,140 A | 6/1934 | Dreyfus |

(Continued)

FOREIGN PATENT DOCUMENTS

| CA | 1146120 A1 | 5/1983 |
| CA | 1272161 A1 | 7/1990 |

(Continued)

OTHER PUBLICATIONS

Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.
(Continued)

*Primary Examiner* — Harry D Wilkins, III
(74) *Attorney, Agent, or Firm* — Suiter Swantz pc llo

(57) ABSTRACT

The present disclosure is a system and method for producing a first product from a first region of an electrochemical cell having a cathode and a second product from a second region of the electrochemical cell having an anode. The method may include a step of contacting the first region with a catholyte comprising carbon dioxide. The method may include another step of contacting the second region with an anolyte comprising a recycled reactant and at least one of an alkane, haloalkane, alkene, haloalkene, aromatic compound, haloaromatic compound, heteroaromatic compound or haloheteroaromatic compound. Further, the method may include a step of applying an electrical potential between the anode and the cathode sufficient to produce a first product recoverable from the first region and a second product recoverable from the second region.

7 Claims, 9 Drawing Sheets

Related U.S. Application Data

(60) Provisional application No. 61/720,670, filed on Oct. 31, 2012, provisional application No. 61/703,158, filed on Sep. 19, 2012, provisional application No. 61/675,938, filed on Jul. 26, 2012, provisional application No. 61/703,229, filed on Sep. 19, 2012, provisional application No. 61/703,175, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(51) Int. Cl.

| | | |
|---|---|---|
| *C25B 3/04* | (2006.01) | |
| *C25B 3/06* | (2006.01) | |
| *C25B 15/08* | (2006.01) | |
| *C07C 51/15* | (2006.01) | |
| *C07C 29/149* | (2006.01) | |
| *C07C 51/02* | (2006.01) | |
| *C25B 1/00* | (2006.01) | |
| *C25B 9/10* | (2006.01) | |
| *C25B 9/08* | (2006.01) | |
| *C25B 1/24* | (2006.01) | |
| *C07C 51/367* | (2006.01) | |
| *C07C 67/08* | (2006.01) | |
| *C07C 1/26* | (2006.01) | |
| *C07C 29/58* | (2006.01) | |
| *C25B 15/00* | (2006.01) | |
| *C25B 13/08* | (2006.01) | |
| *C25B 3/10* | (2006.01) | |

(52) U.S. Cl.
CPC ............ *C07C 51/02* (2013.01); *C07C 51/15* (2013.01); *C07C 51/367* (2013.01); *C07C 67/08* (2013.01); *C25B 1/00* (2013.01); *C25B 1/24* (2013.01); *C25B 3/02* (2013.01); *C25B 3/04* (2013.01); *C25B 3/06* (2013.01); *C25B 9/08* (2013.01); *C25B 9/10* (2013.01); *C25B 13/08* (2013.01); *C25B 15/00* (2013.01); *C25B 15/08* (2013.01); *C25B 3/10* (2013.01); *Y02P 20/127* (2015.11); *Y02P 20/132* (2015.11); *Y02P 20/133* (2015.11); *Y02P 20/582* (2015.11)

(56) References Cited

U.S. PATENT DOCUMENTS

| | | |
|---|---|---|
| 2,060,880 A | 11/1936 | Lazier et al. |
| 3,019,256 A | 1/1962 | Dunn |
| 3,088,990 A | 5/1963 | Rightmire et al. |
| 3,220,941 A | 11/1965 | Osborne et al. |
| 3,236,879 A | 2/1966 | Chiusoli |
| 3,293,292 A | 12/1966 | Olivier et al. |
| 3,326,998 A | 6/1967 | Reusser et al. |
| 3,341,615 A | 9/1967 | Wulf et al. |
| 3,341,616 A | 9/1967 | Vives |
| 3,344,046 A | 9/1967 | Neikam |
| 3,347,758 A | 10/1967 | Koehl, Jr. |
| 3,352,935 A | 11/1967 | Mahan |
| 3,361,653 A | 1/1968 | Miller |
| 3,401,100 A | 9/1968 | Macklin |
| 3,492,209 A | 1/1970 | Miller |
| 3,531,386 A | 9/1970 | Heredy |
| 3,560,354 A | 2/1971 | Young |
| 3,607,962 A | 9/1971 | Krekeler et al. |
| 3,636,159 A | 1/1972 | Solomon |
| 3,720,591 A | 3/1973 | Skarlos |
| 3,745,180 A | 7/1973 | Rennie |
| 3,764,492 A | 10/1973 | Baizer et al. |
| 3,779,875 A | 12/1973 | Michelet |
| 3,824,163 A | 7/1974 | Maget |
| 3,894,059 A | 7/1975 | Selvaratnam |
| 3,959,094 A | 5/1976 | Steinberg |
| 4,072,583 A | 2/1978 | Hallcher et al. |
| 4,087,470 A | 5/1978 | Suzuki |
| 4,088,682 A | 5/1978 | Jordan |
| 4,147,599 A | 4/1979 | O'Leary et al. |
| 4,162,948 A | 7/1979 | Yagii et al. |
| 4,219,392 A | 8/1980 | Halmann |
| 4,245,114 A | 1/1981 | Peltzman |
| 4,253,921 A | 3/1981 | Baldwin et al. |
| 4,256,550 A | 3/1981 | Niinobe et al. |
| 4,267,070 A | 5/1981 | Nefedov et al. |
| 4,299,981 A | 11/1981 | Leonard |
| 4,334,967 A | 6/1982 | Tedoradze et al. |
| 4,343,690 A | 8/1982 | De Nora |
| 4,381,978 A | 5/1983 | Gratzel et al. |
| 4,384,084 A | 5/1983 | Lohse et al. |
| 4,421,613 A | 12/1983 | Goodridge et al. |
| 4,450,055 A | 5/1984 | Stafford |
| 4,476,003 A | 10/1984 | Frank et al. |
| 4,510,214 A | 4/1985 | Crouse et al. |
| 4,523,981 A | 6/1985 | Ang et al. |
| 4,545,886 A | 10/1985 | De Nora et al. |
| 4,547,271 A | 10/1985 | Bharucha et al. |
| 4,560,451 A | 12/1985 | Nielsen |
| 4,563,254 A | 1/1986 | Morduchowitz et al. |
| 4,589,963 A | 5/1986 | Cipriano et al. |
| 4,595,465 A | 6/1986 | Ang et al. |
| 4,608,132 A | 8/1986 | Sammells |
| 4,608,133 A | 8/1986 | Morduchowitz et al. |
| 4,619,743 A | 10/1986 | Cook |
| 4,661,422 A | 4/1987 | Marianowski et al. |
| 4,673,473 A | 6/1987 | Ang et al. |
| 4,702,973 A | 10/1987 | Marianowski |
| 4,732,655 A | 3/1988 | Morduchowitz et al. |
| 4,756,807 A | 7/1988 | Meyer et al. |
| 4,810,596 A | 3/1989 | Ludwig |
| 4,845,252 A | 7/1989 | Schmidt et al. |
| 4,902,828 A | 2/1990 | Wickenhaeuser et al. |
| 4,950,368 A | 8/1990 | Weinberg et al. |
| 4,968,393 A | 11/1990 | Mazur et al. |
| 5,074,974 A | 12/1991 | Toomey, Jr. |
| 5,084,148 A | 1/1992 | Kazcur et al. |
| 5,096,054 A | 3/1992 | Scherson |
| 5,106,465 A | 4/1992 | Kaczur et al. |
| 5,107,040 A | 4/1992 | Repman et al. |
| 5,155,256 A | 10/1992 | Chapman |
| 5,198,086 A | 3/1993 | Chlanda et al. |
| 5,198,311 A | 3/1993 | Nakazawa et al. |
| 5,246,551 A | 9/1993 | Pletcher et al. |
| 5,290,404 A | 3/1994 | Toomey |
| 5,294,319 A | 3/1994 | Kaczur et al. |
| 5,300,369 A | 4/1994 | Dietrich et al. |
| 5,412,150 A | 5/1995 | Wessel |
| 5,443,804 A | 8/1995 | Parker et al. |
| 5,455,372 A | 10/1995 | Hirai et al. |
| 5,474,658 A | 12/1995 | Scharbert et al. |
| 5,514,492 A | 5/1996 | Marincic et al. |
| 5,536,856 A | 7/1996 | Harrison et al. |
| 5,654,493 A | 8/1997 | Wessel |
| 5,804,045 A | 9/1998 | Orillon et al. |
| 5,961,813 A | 10/1999 | Gestermann et al. |
| 6,001,500 A | 12/1999 | Bass et al. |
| 6,024,935 A | 2/2000 | Mills et al. |
| 6,137,005 A | 10/2000 | Honevik |
| 6,171,551 B1 | 1/2001 | Malchesky et al. |
| 6,251,256 B1 | 6/2001 | Blay et al. |
| 6,312,655 B1 | 11/2001 | Hesse et al. |
| 6,348,613 B2 | 2/2002 | Miyamoto et al. |
| 6,380,446 B1 | 4/2002 | Drew et al. |
| 6,465,699 B1 | 10/2002 | Grosso |
| 6,492,047 B1 | 12/2002 | Peled et al. |
| 6,777,571 B2 | 8/2004 | Chaturvedi et al. |
| 6,881,320 B1 | 4/2005 | Krafton et al. |

(56) References Cited

U.S. PATENT DOCUMENTS

| | | |
|---|---|---|
| 6,949,178 B2 | 9/2005 | Tennakoon et al. |
| 7,138,201 B2 | 11/2006 | Inoue et al. |
| 7,462,752 B2 | 12/2008 | Fong et al. |
| 7,883,610 B2 | 2/2011 | Monzyk et al. |
| 8,227,127 B2 | 7/2012 | Little et al. |
| 8,277,631 B2 | 10/2012 | Eastman et al. |
| 8,313,634 B2 | 11/2012 | Bocarsly et al. |
| 8,444,844 B1 | 5/2013 | Teamey et al. |
| 8,562,811 B2 | 10/2013 | Sivasankar et al. |
| 8,663,447 B2 | 3/2014 | Bocarsly et al. |
| 8,721,866 B2 | 5/2014 | Sivasankar et al. |
| 9,090,976 B2 | 7/2015 | Bocarsly et al. |
| 2001/0001798 A1 | 5/2001 | Sharpless et al. |
| 2001/0026884 A1 | 10/2001 | Appleby et al. |
| 2002/0013477 A1 | 1/2002 | Kim et al. |
| 2002/0022753 A1 | 2/2002 | Drew et al. |
| 2002/0122980 A1 | 9/2002 | Fleischer et al. |
| 2004/0006246 A1 | 1/2004 | Sherman et al. |
| 2004/0115489 A1 | 6/2004 | Goel |
| 2005/0139486 A1 | 6/2005 | Carson et al. |
| 2005/0245784 A1 | 11/2005 | Carson et al. |
| 2006/0102468 A1 | 5/2006 | Monzyk et al. |
| 2006/0269813 A1 | 11/2006 | Seabaugh et al. |
| 2007/0004023 A1 | 1/2007 | Trachtenberg et al. |
| 2007/0012577 A1 | 1/2007 | Bulan et al. |
| 2007/0224479 A1 | 9/2007 | Tadokoro et al. |
| 2008/0223727 A1 | 9/2008 | Oloman et al. |
| 2008/0245660 A1 | 10/2008 | Little et al. |
| 2008/0248350 A1 | 10/2008 | Little et al. |
| 2008/0283411 A1 | 11/2008 | Eastman et al. |
| 2008/0286643 A1 | 11/2008 | Iwasaki |
| 2008/0296146 A1 | 12/2008 | Toulhoat et al. |
| 2008/0314758 A1 | 12/2008 | Grosso |
| 2009/0000956 A1 | 1/2009 | Weidner et al. |
| 2009/0014336 A1 | 1/2009 | Olah et al. |
| 2009/0030240 A1 | 1/2009 | Olah et al. |
| 2009/0057161 A1 | 3/2009 | Aulich et al. |
| 2009/0062110 A1 | 3/2009 | Koshino et al. |
| 2009/0156867 A1 | 6/2009 | Van Kruchten |
| 2009/0308759 A1 | 12/2009 | Waycuilis |
| 2010/0051859 A1 | 3/2010 | House et al. |
| 2010/0061922 A1 | 3/2010 | Rauser et al. |
| 2010/0069600 A1 | 3/2010 | Morelle et al. |
| 2010/0130768 A1 | 5/2010 | Sato et al. |
| 2010/0140103 A1 | 6/2010 | Gilliam et al. |
| 2010/0187123 A1 | 7/2010 | Bocarsly et al. |
| 2010/0187125 A1 | 7/2010 | Sandoval et al. |
| 2010/0191024 A1 | 7/2010 | Uenveren et al. |
| 2010/0196800 A1 | 8/2010 | Markoski et al. |
| 2010/0248042 A1 | 9/2010 | Nakagawa et al. |
| 2010/0270167 A1 | 10/2010 | McFarland |
| 2010/0282614 A1 | 11/2010 | Detournay et al. |
| 2010/0305629 A1 | 12/2010 | Lund et al. |
| 2010/0330435 A1 | 12/2010 | Nemeth et al. |
| 2011/0024288 A1 | 2/2011 | Bhavaraju et al. |
| 2011/0083968 A1 | 4/2011 | Gilliam et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0143224 A1 | 6/2011 | Rittmann et al. |
| 2011/0143929 A1 | 6/2011 | Sato et al. |
| 2011/0177398 A1 | 7/2011 | Affinito et al. |
| 2011/0186441 A1 | 8/2011 | LaFrancois et al. |
| 2011/0217226 A1 | 9/2011 | Mosa et al. |
| 2011/0226632 A1 | 9/2011 | Cole et al. |
| 2011/0237830 A1 | 9/2011 | Masel |
| 2011/0303551 A1 | 12/2011 | Gilliam et al. |
| 2011/0318617 A1 | 12/2011 | Kirchev et al. |
| 2012/0004448 A1 | 1/2012 | Bhattacharyya et al. |
| 2012/0004449 A1 | 1/2012 | Bhattacharyya |
| 2012/0004454 A1 | 1/2012 | Bhattacharyya et al. |
| 2012/0018311 A1 | 1/2012 | Yotsuhashi et al. |
| 2012/0043301 A1 | 2/2012 | Arvin et al. |
| 2012/0132537 A1 | 5/2012 | Sivasankar et al. |
| 2012/0132538 A1 | 5/2012 | Cole et al. |
| 2012/0199493 A1 | 8/2012 | Krafft et al. |
| 2012/0215034 A1 | 8/2012 | McFarland |
| 2012/0228147 A1 | 9/2012 | Sivasankar et al. |
| 2012/0277465 A1 | 11/2012 | Cole et al. |
| 2012/0292196 A1 | 11/2012 | Albrecht et al. |
| 2012/0295172 A1 | 11/2012 | Peled et al. |
| 2012/0298522 A1 | 11/2012 | Shipchandler et al. |
| 2012/0329657 A1 | 12/2012 | Eastman et al. |
| 2013/0062216 A1 | 3/2013 | Yotsuhashi et al. |
| 2013/0098772 A1 | 4/2013 | Bocarsly et al. |
| 2013/0105304 A1 | 5/2013 | Kaczur et al. |
| 2013/0105330 A1 | 5/2013 | Teamey et al. |
| 2013/0118907 A1 | 5/2013 | Deguchi et al. |
| 2013/0118909 A1 | 5/2013 | Kaczur et al. |
| 2013/0118911 A1 | 5/2013 | Sivasankar et al. |
| 2013/0134048 A1 | 5/2013 | Teamey et al. |
| 2013/0134049 A1 | 5/2013 | Teamey et al. |
| 2013/0137898 A1 | 5/2013 | Teamey et al. |
| 2013/0140187 A1 | 6/2013 | Teamey et al. |
| 2013/0180863 A1 | 7/2013 | Kaczur et al. |
| 2013/0180865 A1 | 7/2013 | Cole et al. |
| 2013/0186771 A1 | 7/2013 | Zhai et al. |
| 2013/0199937 A1 | 8/2013 | Cole et al. |

FOREIGN PATENT DOCUMENTS

| | | |
|---|---|---|
| CA | 2043256 A1 | 12/1991 |
| CA | 2391938 A1 | 5/2001 |
| CN | 101743343 A | 6/2010 |
| CN | 102190573 A | 9/2011 |
| DE | 1047765 A | 12/1958 |
| DE | 2301032 A | 7/1974 |
| EP | 0028430 A1 | 5/1981 |
| EP | 2329875 A1 | 6/2011 |
| FR | 853643 | 3/1940 |
| GB | 1096847 A | 12/1967 |
| GB | 1223452 A | 2/1971 |
| GB | 1285209 A | 8/1972 |
| GB | 1584524 A | 4/1977 |
| GB | 2038335 A | 7/1980 |
| GB | 2312218 A | 10/1997 |
| JP | 48029721 | 4/1973 |
| JP | 50052010 | 5/1975 |
| JP | 53101311 | 4/1978 |
| JP | 64-015388 | 1/1989 |
| JP | 7-75784 | 10/1996 |
| JP | 7-118886 | 10/1996 |
| JP | 2000104190 | 4/2000 |
| JP | 2004533545 | 11/2004 |
| JP | 2009540130 | 11/2009 |
| JP | 2012516392 A | 7/2012 |
| WO | 91/01947 A1 | 2/1991 |
| WO | WO 9724320 A1 | 7/1997 |
| WO | 9850974 A1 | 11/1998 |
| WO | WO 0015586 A1 | 3/2000 |
| WO | WO0138275 A1 | 5/2001 |
| WO | 03004727 A2 | 1/2003 |
| WO | WO 200467673 A1 | 8/2004 |
| WO | 2006074335 A2 | 7/2006 |
| WO | 2007041872 A1 | 4/2007 |
| WO | WO 2007041872 A1 | 4/2007 |
| WO | 2007/091616 A1 | 8/2007 |
| WO | 2007145586 A1 | 12/2007 |
| WO | 2009012154 A2 | 1/2009 |
| WO | 2009108327 A1 | 9/2009 |
| WO | 2011069008 | 6/2011 |
| WO | 2011116236 A2 | 9/2011 |
| WO | 2011160577 A1 | 12/2011 |
| WO | 2012015921 A1 | 2/2012 |
| WO | WO 2012046362 A1 | 4/2012 |
| WO | 2012118065 A1 | 9/2012 |
| WO | 2012166997 A2 | 12/2012 |

OTHER PUBLICATIONS

Wu et al., "Electrochemical Reduction of Carbon Dioxide I. Effects of the Electrolyte on the Selectivity and Activity with Sn Electrode",

(56) References Cited

OTHER PUBLICATIONS

Journal of the Electrochemical Society (no month, 2012), vol. 159, No. 7, pp. F353-F359.
Chaplin et al., "Effects of Process Conditions and Electrode Material on Reaction Pathways for Carbon Dioxide Electroreduction with Particular Reference to Formate Formation", Journal of Applied Electrochemistry (no month, 2003), vol. 33, pp. 1107-1123.
Jaime-Ferrer et al., "Three-Compartment Bipolar Membrane Electrodialysis for Splitting of Sodium Formate into Formic Acid and Sodium Hydroxide: Role of Diffusion of Molecular Acid", Journal of Membrane Science (no month, 2008), vol. 325, pp. 528-536.
Seshadri et al, "A new homogeneous catalyst for the reduction of carbon dioxide to methanol at low overpotential," Journal of Electroanalytical Chemistry, 372 (1994) 145-150.
Hori et al, chapter on "Electrochemical CO2 Reduction on Metal Electrodes," in the book "Modern Aspects of Electrochemistry," vol. 42, pp. 106 and 107.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.
James Grimshaw, Electrochemical Reactions and Mechanisms in Organic Chemistry, 2000, ISBN 978-0-444-72007-8. [retrieved on Jan. 3, 2014]. Retrieved from the Internet. <URL: http://f3.tiera.ru/ShiZ/Great%20Science%20TextBooks/Great%Science%20Textbooks%20DVD%20Library%202007%20-%20Supplement%20Five/Chemistry/Organic%20Chemistry/Electrochemical%20Reactions%20and%20Mechanisms%20in%20Organic%20Chemistry%20-%20J.%20Grimshaw%20%28Elsevier,%202000%29%WW.pdf>.
Fischer, J. et al. "The production of oxalic acid from CO2 and H2O." Journal of Applied Electrochemistry, 1981, vol. 11, pp. 743-750.
Goodridge, F. et al., The electrolytic reduction of carbon dioxide and monoxide for the production of carboxylic acids.: Journal of applied electrochemistry, 1984, vol. 14, pp. 791-796.
Scibioh et al, "Electrochemical Reduction of Carbon Dioxide: A Status Report," Proc. Indian Natn Science Acad., 70, A, No. 3, May 2004, pp. 407-762.
Hori et al, "Enhanced Formation of Ethylene and Alcohols at Ambient Temperature and Pressure in Electrochemical Reduction of Carbon Dioxide at a Copper Electrode," J. Chem. Soc. Chem. Commun. (1988), pp. 17-19.
Hossain et al, "Palladium and Cobalt Complexes of Substituted Quinoline, Bipyridine and Phenanthroline as Catalysts for Electrochemical Reduction of Carbon Dioxide," Electrochimica Acta, vol. 42, No. 16 (1997), pp. 2577-2585.
Fischer, "Liquid Fuels from Water Gas", Industrial and Engineering Chemistry, vol. 17, No. 6, Jun. 1925, pp. 574-576.
Williamson et al, "Rate of Absorption and Equilibrium of Carbon Dioxide in Alkaline Solutions", Industrial and Engineering Chemistry, vol. 16, No. 11, Nov. 1924, pp. 1157-1161.
Hori, "Electrochemical CO2 Reduction on Metal Electrodes", Modern Aspects of Electrochemistry, No. 42, 2008, pp. 89-189.
Green et al., "Vapor-Liquid Equilibria of Formaldehyde-Methanol-Water", Industrial and Engineering Chemistry (Jan. 1955), vol. 47, No. 1, pp. 103-109.
Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.
Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).
Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.
Perez et al., "Activation of Carbon Dioxide by Bicyclic Amidines", J. Org. Chem. (no month, 2004), vol. 69, pp. 8005-8011.
Tinnemans et al., "Tetraaza-macrocyclic cobalt(II) and nickel(II) complexes as electron-transfer agents in the photo (electro)chemical and electrochemical reduction of carbon dioxide," Recl.Tray. Chim. Pays-Bas, Oct. 1984, 103: 288-295.
Bocarsly et al., "Photoelectrochemical conversion of carbon dioxide to methanol and higher alcohols, a chemical carbon sequestration strategy," Preprints of Symposia—American Chemical Society, Division of Fuel Chemistry, Volume: 53, Issue: 1, pp. 240-241.
Chen et al., "Tin oxide dependence of the CO2 reduction efficiency on tin electrodes and enhanced activity for tin/tin oxide thin-film catalysts." Journal of the American Chemical Society 134, No. 4 (2012): 1986-1989, Jan. 9, 2012, retrieved on-line.
Zhou et al. "Anodic passivation processes of indium in alkaline solution [J]" Journal of Chinese Society for Corrosion and Protection 1 (2005): 005, Feb. 2005.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258.
Nefedov and Manov-Yuvenskii, The Effect of Pyridine Bases and Transition-Metal Oxides on the Activity of PdCl2 in the Carbonylation of Aromatic Mononitro Compounds by Carbon Monoxide, 28 Bulletin of the Acad. Of Sciences of the USSR 3, 540-543 (1979).
Vojinovic "Bromine oxidation and bromine reduction in propylene carbonate" Journal of Electroanalytical Chemistry, 547 (2003) p. 109-113.
Babic et al (Electrochimica Acta, 51, 2006, 3820-3826).
Yoshida et al. (Journal of Electroanalytical Chemistry, 385, 1995, 209-225).
Seshadri et al., A New Homogeneous Electrocatalyst for the Reduction of Carbon Dioxide to Methanol at Low Overpotential, Journal of Electroanalytical Chemistry, 372 (1994), 145-50.
Green et al., Vapor-Liquid Equilibria of Formaldehyde-Methanol-Water, Industrial and Engineering Chemistry (Jan. 1955), vol. 47, No. 1, pp. 103-109.
Scibioh et al., Electrochemical Reduction of Carbon Dioxide: A Status Report, Proc Indian Natn Sci Acad (May 2004), vol. 70, A, No. 3, pp. 407-462.
Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.
Perez et al., Activation of Carbon Dioxide by Bicyclic Amidines, J. Org. Chem. (no month, 2004), vol. 69, pp. 8005-8011.
Zaragoza Dorwald, Side Reactions in Organic Synthesis, 2005, Wiley-Vch Verlag GmbH & Co. KGaA, Weinheim, Preface. p. IX.
Liansheng et al, Journal of South Central University Technology, Electrode Selection of Electrolysis with Membrane for Sodium Tungstate Solution, 1999, 6(2), pp. 107-110.
Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.
Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.

(56) References Cited

OTHER PUBLICATIONS

B. Eneau-Innocent et al., Electroreduction of carbon dioxide at a lead electrode in propylene carbonate: A spectroscopic study, Applied Catalysis B: Environmental 98 (2010) 65-71.
Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.
S. Gambino and G. Silvestri, On the electrochemical reduction of carbon dioxide and ethylene, Tetrahedron Letters No. 32, pp. 3025-3028, 1973, Pergamon Press, Printed in Great Britain.
K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.
A. Sepulveda-Escribano et al., Platinum catalysts supported on carbon blacks with different surface chemical properties, Applied Catalysis A: General, 173, 1998, p. 247-257.
F.M. Al Kharafi et al., Electrochemical Oxidation of Sulfide Ions on Platinum Electrodes, Modern Applied Science, vol. 4, No. 3, Mar. 2010, pp. 2-11.
P.W.T. Lu, et al., Recent developments in the technology of sulphur dioxide depolarized electrolysis, Journal of Applied Electrochemistry, vol. 11, No. 3, May 1981, pp. 347-355.
Seshadri, Part I Electrocatalysis at modified semiconductor and metal electrodes; Part II Electrochemistry of nickel and cadmium hexacyanoferrates, Diss. Abstr. Int. B 1994, 54(12, Pt. 1), 6198, pp. 52-85.
Cuihong Yan et al., The Lastest Research Progress of Electrocatalytic Reduction Product of CO2, Chemical Engineer, Issue 7, p. 42-45, Jul. 25, 2010.
Yingchu Tao et al., Research Progress of Electrochemical Reduction of Carbon Dioxide, Chemistry, Issue 5, p. 272-277, Dec. 31, 2001, http://chemistrymag.org.
Wenying Wei et al., The research progress of CO2 electrocatalysis in water soluble medium, Progress in Chemistry, col. 26, Issue 2, 4 pages, Dec. 2008.
Matayoshi et al., Electrochemical Reforming of CH4-O02 Gas Using Porous Gd-Doped Ceria Electrolyte with Ni and Ru Electrodes, Journal of the Ceramic Society of Japan, vol. 117, 2009, pp. 1107-1112, Abstract Only.
Koeleli et al., Electrochemical Reduction of CO2 at Pb- and Sn-Electrodes in a Fixed-Bed Reactor in Aqueous K2CO3 and KHCO3 Media, Journal of Applied Electrochemistry, vol. 33, No. 5, 2003, pp. 447-450, Abstract Only.
Cao et al., Electrocatalytic Reduction of Carbon Dioxide Using Cobalt Tetrakis(4-Trimethylammoniophenyl)porphyrin Iodide Under High Pressure, Huazue Xuebao, vol. 44, No. 3, 1986, pp. 220-224, Abstract Only.
T. Meisel et al., The thermal decomposition of alkali metal formates, Journal of Thermal Analysis, vol. 7, No. 1, Feb. 1, 1975, pp. 73-80.
Cole, EB et al., Using a One-Electron Shuttle for the Multielectron Reduction of CO2 to Methanol: Kinetic, Mechanistic, and Structural Insights, Journal of the American Chemical Society, Jul. 28, 2010, vol. 132, pp. 11539-11551.
Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.
M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.
Afroza Begum, Electrochemical CO2 Reduction, Thesis, 2011, University of Newfoundland, http://collections.mun.ca/cdm4/document.php?CISOROOT=/theses5&CISOPTR=14718&REC=7.
Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 4701-4706.
Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.
Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.
Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.
Fisher et al., "Electrocatalytic reduction of carbon dioxide by using macrocycles of nickel and cobalt", Journal of the American Chemical Society, vol. 102, No. 24, Sep. 1, 1980, pp. 7361-7363.
Ishida et al., Selective Formation of HC00—In the Electrochemical CO2 Reduction Catalyzed by URU(BPY)2(CO)2 3/4 2+ (BPY = 2,2'-Bipyridine), Journal of the Chemical Society, Chemical Communications, Chemical Society, Letchworth, GB, Jan. 1, 1987, pp. 131-132.
Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.
Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258. 1-page abstract only.
Li et al., "the Electro-Reduction of Carbon Dioxide in a Continuous Reactor", J. of Applied Electrochemistry (no month, 2005), vol. 35, pp. 955-965.
Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.
Yuan et al., "Electrochemical Activation of Carbon Dioxide for Synthesis of Dimethyl Carbonate in an Ionic Liquid", Electrochimica Acta (no month, 2009), vol. 54, pp. 2912-2915.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.

ELECTROCHEMICAL CO-PRODUCTION OF PRODUCTS WITH CARBON-BASED REACTANT FEED TO ANODE

CROSS-REFERENCE TO RELATED APPLICATIONS

The present application claims the benefit under 35 U.S.C. §120 of U.S. patent application Ser. No. 13/724,647 filed Dec. 21, 2012. Said U.S. patent application Ser. No. 13/724,647 filed Dec. 21, 2012 is hereby incorporated by reference in its entirety.

The U.S. patent application Ser. No. 13/724,647 filed Dec. 21, 2012 claims the benefit under 35 U.S.C. §119(e) of U.S. Provisional Application Ser. No. 61/720,670 filed Oct. 31, 2012, U.S. Provisional Application Ser. No. 61/703,158 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,158 filed Sep. 19, 2012 and U.S. Provisional Application Ser. No. 61/675,938 filed Jul. 26, 2012 are incorporated by reference in their entireties.

The U.S. patent application Ser. No. 13/724,647 filed Dec. 21, 2012 also claims the benefit under 35 U.S.C. §119(e) of U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012, U.S. Provisional Application Ser. No. 61/703,187 filed Sep. 19, 2012. The U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

The present application incorporates by reference co-pending U.S. patent application Ser. No. 13/724,339 filed Dec. 21, 2012, U.S. patent application Ser. No. 13/724,878 filed Dec. 21, 2012, U.S. patent application Ser. No. 13/724,647 filed Dec. 21, 2012, U.S. patent application Ser. No. 13/724,231 filed Dec. 21, 2012, U.S. patent application Ser. No. 13/724,996 filed Dec. 21, 2012, U.S. patent application Ser. No. 13/724,719 filed Dec. 21, 2012, U.S. patent application Ser. No. 13/724,082 filed Dec. 21, 2012 and U.S. patent application Ser. No. 13/724,768 filed Dec. 21, 2012 now U.S. Pat. No. 8,444,844 in their entireties.

TECHNICAL FIELD

The present disclosure generally relates to the field of electrochemical reactions, and more particularly to methods and/or systems for electrochemical co-production of chemicals with a carbon-based reactant feed to anode.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY OF THE PREFERRED EMBODIMENTS

The present disclosure includes a system and method for producing a first product from a first region of an electrochemical cell having a cathode and a second product from a second region of the electrochemical cell having an anode. The method may include a step of contacting the first region with a catholyte comprising carbon dioxide. The method may include another step of contacting the second region with an anolyte comprising a recycled reactant and at least one of an alkane, haloalkane, alkene, haloalkene, aromatic compound, haloaromatic compound, heteroaromatic compound or halo-heteroaromatic compound. Further, the method may include a step of applying an electrical potential between the anode and the cathode sufficient to produce a first product recoverable from the first region and a second product recoverable from the second region.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1-6, systems and methods of electrochemical co-production of products with a carbon-based reactant feed to an anode are disclosed. It is contemplated that the electrochemical co-production of products may include a production of a first product, such as reduction of carbon dioxide to carbon-based products to include one, two, three, and four carbon chemicals, at a cathode side of an electrochemical cell with co-production of a second product, such as an oxidized carbon-based product, at the anode of the electrochemical cell where the anolyte comprises a carbon-based reactant and a recycled reactant, where the recycled reactant is preferably a halide AX. AX may be a compound where A is H, Li, Na, K, Cs, Mg, Ca, or other metal, or $R_4R^+$, $R_4N^+$—where each R is independently alkyl or aryl—or a cation; and X is F, Cl, Br, I, ClO4-, PF6-, BF4-, or an anion; and mixtures thereof.

A carbon-based reactant may include an oxidizable carbon compound. Carbon-based reactants may include, for example, methane, ethane, ethylene, benzene, toluene, xylene, ethylbenzene, propane, propene, butane, 1-butene, 2-butene, isobutane, ethyl acetate, propionitrile, methyl propionate, ethyl propionate, other alkanes, substituted alkanes, haloalkanes, alkenes, substituted alkenes, haloalkenes, aromatic, haloaromatic, heteroaromatic, and halo-heteroaromatic compounds.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1:
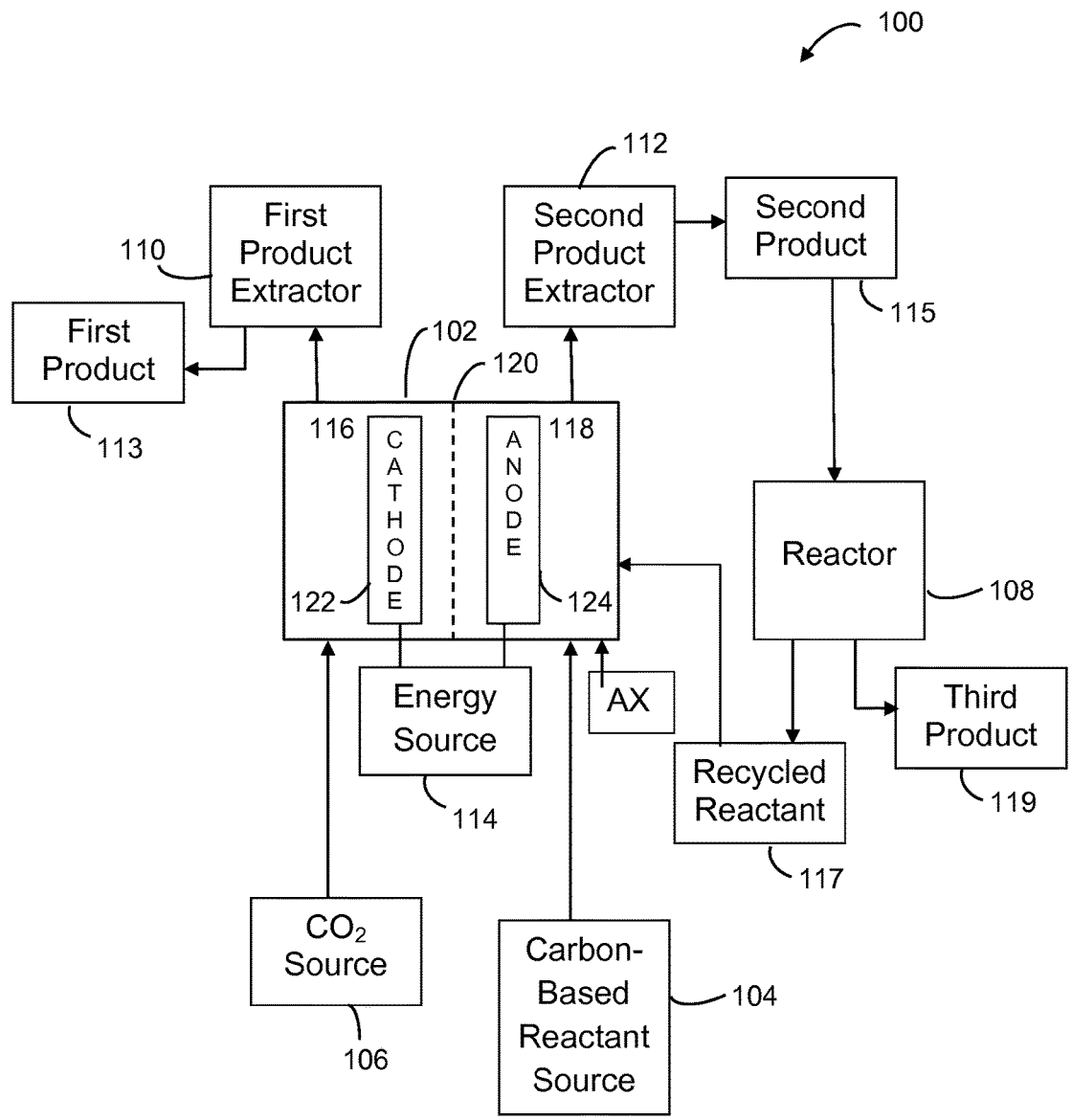
FIG. 1 is a block diagram of a system in accordance with an embodiment of the present disclosure.

Referring to FIG. 1, a block diagram of a system 100 in accordance with an embodiment of the present disclosure is shown. System (or apparatus) 100 generally includes an electrochemical cell (also referred as a container, electrolyzer, or cell) 102, a carbon-based reactant source 104, a carbon dioxide source 106, a reactor 108, a first product extractor 110 and a first product 113, a second product extractor 112, second product 115, and an energy source 114.

Electrochemical cell 102 may be implemented as a divided cell. The divided cell may be a divided electrochemical cell and/or a divided photoelectrochemical cell. Electrochemical cell 102 may include a first region 116 and a second region 118. First region 116 and second region 118 may refer to a compartment, section, or generally enclosed space, and the like without departing from the scope and intent of the present disclosure. First region 116 may include a cathode 122. Second region 118 may include an anode 124. First region 116 may include a catholyte whereby carbon dioxide is dissolved in the catholyte. Second region 118 may include an anolyte which may include a carbon-based reactant and a recycled reactant. A source of AX may be operably connected to second region 118. Energy source 114 may generate an electrical potential between the anode 124 and the cathode 122. The electrical potential may be a DC voltage. Energy source 114 may be configured to supply a variable voltage or constant current to electrochemical cell 102. Separator 120 may selectively control a flow of ions between the first region 116 and the second region 118. Separator 120 may include an ion conducting membrane or diaphragm material.

Electrochemical cell 102 is generally operational to reduce carbon dioxide in the first region 116 to a first product 113 recoverable from the first region 116 while producing a second product 115 recoverable from the second region 118. Cathode 122 may reduce the carbon dioxide into a first product 113 that may include one or more compounds. Examples of the first product 113 recoverable from the first region by first product extractor 110 may include CO, formic acid, formaldehyde, methanol, methane, oxalate, oxalic acid, glyoxylic acid, glyoxylate, glycolic acid, glycolate, glyoxal, glycolaldehyde, ethylene glycol, acetic acid, acetate, acetaldehyde, ethanol, ethane, ethylene, lactic acid, lactate, propanoic acid, propionate, acetone, isopropanol, 1-propanol, 1,2-propylene glycol, propane, propylene, 1-butanol, 2-butanone, 2-butanol, butane, butane, a carboxylic acid, a carboxylate, a ketone, an aldehyde, and an alcohol.

Carbon dioxide source 106 may provide carbon dioxide to the first region 116 of electrochemical cell 102. In some embodiments, the carbon dioxide is introduced directly into the region 116 containing the cathode 122. It is contemplated that carbon dioxide source may include a source of multiple gases in which carbon dioxide has been filtered from the multiple gases.

First product extractor 110 may implement an organic product and/or inorganic product extractor. First product extractor 110 is generally operational to extract (separate) the first product 113 from the first region 116. The extracted first product 113 may be presented through a port of the system 100 for subsequent storage and/or consumption by other devices and/or processes.

The anode side of the reaction occurring in the second region 118 may include a carbon-based reactant, which may be a gas phase, liquid phase, or solution phase reactant, and a recycled reactant supplied to the second region 118. The second product 115 recoverable from the second region 118 may be derived from a variety of oxidations such as the oxidation of an organic chemical of the carbon-based reactant to another organic chemical product. Oxidations may be direct, such as the conversion of ethane to ethanol at the anode. They also may be indirect, such as conversion of ethane to ethanol utilizing a halogen produced at the anode. Recycled reactant may include a hydrogen halide or halide salt that may be recovered from the second product 115 via another reactor 108. For example, the recycled reactant may include AX where A is H, Li, Na, K, Cs, Mg, Ca, or other metal, or $R_4P^+$, $R_4N^+$—where each R is independently alkyl or aryl—or a cation; and X is F, Cl, Br, I, or an anion; and mixtures thereof. Examples are in the table below.

TABLE 1

| Chemical Feed to Anode | Oxidation Product(s) |
| --- | --- |
| Methane | Methanol, methyl bromide, chloroform |
| Methanol | Dibromomethane, formaldehyde, alpha bromoethers, dialkoxy methane |

TABLE 1-continued

| Chemical Feed to Anode | Oxidation Product(s) |
| --- | --- |
| Ethane | Ethyl Bromide, Ethanol, ethylene or other C2 chemicals |
| Ethene (Ethylene) | Vinyl chloride, vinyl bromide, tetrafluoroethylene |
| Propane | Propyl bromide, Propylene, Propanol or other C3 chemicals |
| Propene | Allyl bromide, allyl alcohol, allyl halide, other C3 chemicals |
| Butane | Butyl bromide, butene, butadiene, butanol, or other C4 chemicals |
| Butene | Butadiene, halo-1-butenes, halo-2-butenes, other halo-C4 chemicals |
| Isobutane | Isobutylene, halo-isobutylenes, isobutyl alcohols |
| Ethylbenzene | Styrene |
| Ethyl acetate | Vinyl acetate |
| Methyl propionate, Ethyl propionate | Methyl acrylate, ethyl acrylate |
| Propionitrile | Acrylonitrile |
| Benzene | Chlorobenzene, bromobenzene, Phenol |
| Toluene | Benzyl alcohol, benzaldehyde, benzoic acid |
| Xylene | Terephthalic acid |
| Alkanes | Haloalkanes, polyhaloalkanes, perhaloalkanes |
| Haloalkanes | Polyhaloalkanes, perhaloalkanes |
| Alkenes | Haloalkenes, polyhaloalkenes, perhaloalkenes |
| Haloalkenes | Polyhaloalkenes, perhaloalkenes |
| Halides ($F^-$, $Cl^-$, $Br^-$, $I^-$) | Halogens ($F_2$, $Cl_2$, $Br_2$, $I_2$) |
| Hydrogen halides (HF, HCl, HBr, HI) | Halogens ($F_2$, $Cl_2$, $Br_2$, $I_2$) |

Second product extractor 112 may extract the second product 115 from the second region 118. The extracted second product 115 may be presented through a port of the system 100 for subsequent storage and/or consumption by other devices and/or processes. It is contemplated that first product extractor 110 and/or second product extractor 112 may be implemented with electrochemical cell 102, or may be remotely located from the electrochemical cell 102. Additionally, it is contemplated that first product extractor 110 and/or second product extractor 112 may be implemented in a variety of mechanisms and to provide desired separation methods, such as fractional distillation, without departing from the scope and intent of the present disclosure.

Furthermore, second product 115 may be presented to another reactor, such as a reactor 108, where a recycled reactant 117 is a byproduct of a reaction of the second product 115 recovered from the second region 118 of the electrochemical cell 102. A third product 119 produced by reactor 108 as an additional byproduct of a reaction at reactor 108 may include an alcohol, alkene or various other types of compounds. Recycled reactant 117 may be recycled back to the second region 118 as an input feed to the second region 118 of electrochemical cell 102. It is contemplated that an additional source of recycled reactant may be further supplied as an input feed to the second region 118 of the electrochemical cell 102 without departing from the scope and intent of the present disclosure.

Through the co-production of a first product 113 and a second product 115, the overall energy requirement for making each of the first product 113 and second product 115 may be reduced by 50% or more. In addition, electrochemical cell 102 may be capable of simultaneously producing two or more products with high selectivity.

Figure 2A:
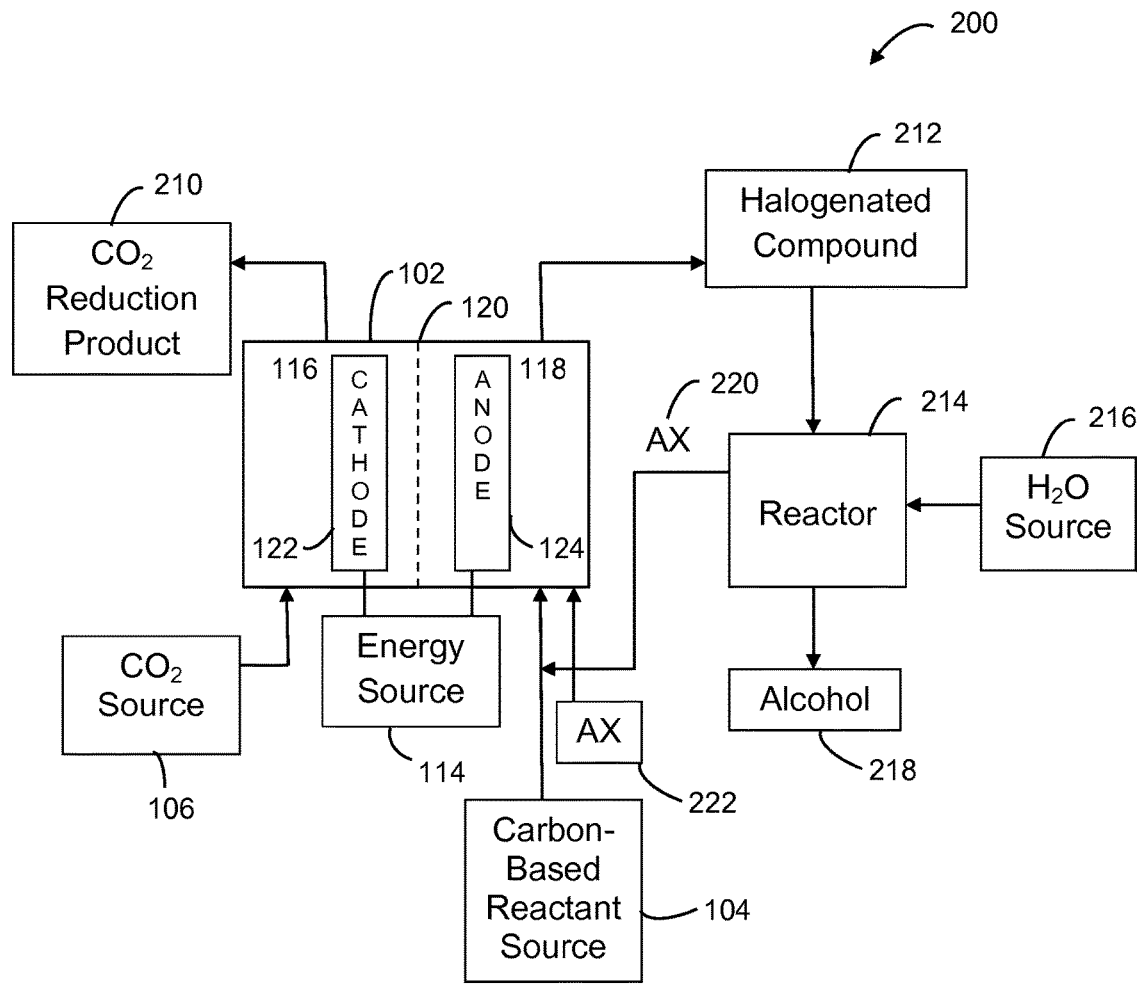
FIG. 2A is a block diagram of a system in accordance with another embodiment of the present disclosure.

A preferred embodiment of the present disclosure may include production of organic chemicals, such as carbon dioxide reduction products, at the cathode while simultaneously using a hydrogen halide or halide salt feed to the anode for use in the indirect oxidation of carbon-based reactants. Referring to FIG. 2A, system 200 for co-production of a carbon dioxide reduction product 210 and an alcohol 218, through a halogenated compound 212 is shown. The oxidation of AX 220 where A is H, Li, Na, K, Cs, Mg, Ca, or other metal, or $R_4P^+$, $R_4N^+$—where each R is independently alkyl or aryl—or a cation; and X is F, Cl, Br, I, or an anion; and mixtures thereof (hereinafter generally referred as AX), produces protons and electrons that are utilized to reduce carbon dioxide. A resulting halogen from the oxidation reaction at the second region 118, such as $Br_2$, may be reacted with a carbon-based reactant, such as ethane or propane, provided by carbon-based reactant source 104 to selectively produce a halogenated compound 212. Halogenated compound 212, such as bromoethane, may be isolated, or it may be supplied to reactor 214 that may react with water from water source 216 to produce an alcohol 218, such as ethanol. While alcohol 218 is shown, it is contemplated that various types of other products may also be produced via reactor 214, such as an alkene. In one embodiment, a byproduct of the halogenation of an alkane supplied by carbon-based reactant source 104 and subsequent conversion to an alcohol 218 is a recycled reactant 220, such as hydrogen bromide.

AX 220 may be recycled back to the second region 118 of the electrochemical cell 102 either as a pure anhydrous gas or in a liquid phase. The gas phase may be generally preferred in order to minimize energy requirements. Bromine or a similar halogen is thereby recycled, while a carbon dioxide reduction product 210 is produced at the first region 116 from $CO_2$. The halogen is thus used both to oxidize carbon-based reactants, such as alkanes, alkenes and aromatic compounds, to a desired product and to transfer hydrogen ions or protons from the carbon-based reactant to the first region for $CO_2$ reduction. The carbon-based reactant may serve as the primary hydrogen source for $CO_2$ reduction. It is contemplated that an additional source of AX 222 may be further supplied in addition to the recycled reactant AX 220 as an input feed to the second region 118 of the electrochemical cell 102 without departing from the scope and intent of the present disclosure.

System 200 of FIG. 2 may be employed with various types of carbon-based reactants, including various types of alkanes, alkenes and aromatic compounds to produce various types of products (first product and second product) as desired and shown in an exemplary fashion in Table 1. Furthermore, a halogenated compound 212 may be further converted to various types of products, including a perhalocarbon, vinyl chloride, dichloroethane, allyl chloride, chlorophenol, bromobenzene, vinyl bromide, vinyl fluoride, vinylidene fluoride, tetrafluoroethylene, hexafluoropropylene, difluoromethane, or pentafluoroethane. It is further contemplated that other types of products may be co-produced by the anode and cathode of an electrochemical cell without departing from the scope and intent of the present disclosure.

Figure 2B:
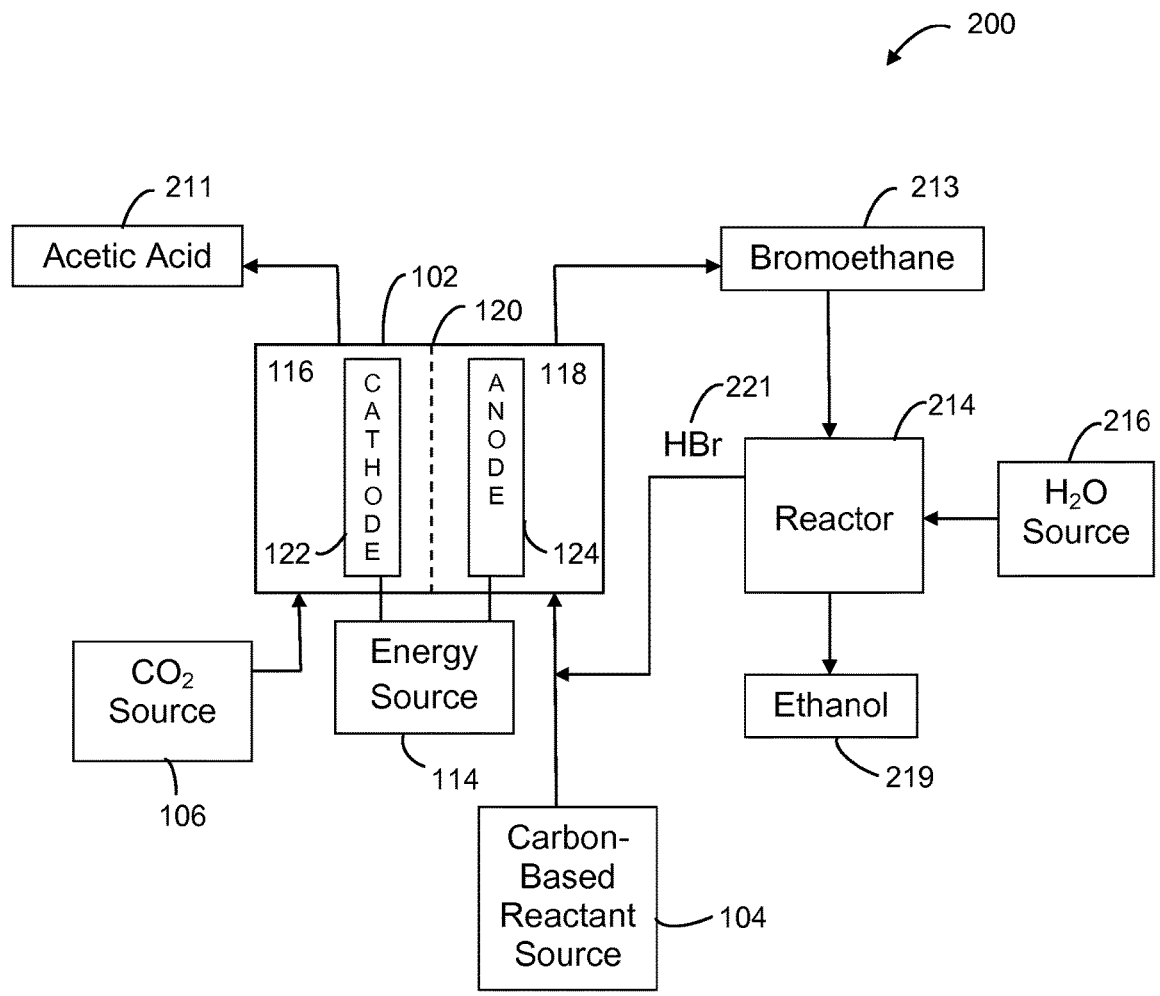
FIG. 2B is a block diagram of a system in accordance with an additional embodiment of the present disclosure.

Referring to FIG. 2B, a block diagram of a system 200 in accordance with an additional embodiment of the present disclosure. Similar to the embodiment shown in FIG. 2A, FIG. 2B is a block diagram of a system in accordance with an additional embodiment of the present disclosure wherein carbon-based reactant source may supply an alkane, such as ethane and the halogenated compound produced at second region 118 may be bromoethane 213. The carbon-dioxide reduction product may be acetic acid 211. Bromoethane 213 may be supplied to reactor 214 and reacted with water from water source 216 to produce HBr 221 which is recycled as an input feed to the first region 118 and ethanol 219. In one embodiment of the disclosure, when the carbon dioxide reduction product is acetic acid 211 and ethane is provided by carbon-based reactant source 104, then the molar ratios of the product may be 1 acetic acid: 4 ethanol because acetic acid production from $CO_2$ is an 8 electron process and ethanol from ethane is a two electron process. The mass ratios may be 1:3.

It is contemplated that reactions occurring at the first region 116 may occur in a catholyte which may include water, methanol, acetonitrile, propylene carbonate, ionic liquids, or other catholytes. The reactions occurring at the second region 118 may be in a gas phase, for instance in the case of gas phase reactant 118 such as methane or a hydrogen halide. The reaction at the second region 118 may also occur in liquid phase, such as the case of a halide in solution.

In another embodiment, the second region 118 reaction may include an introduction of gas phase benzene into anolyte with gaseous HBr, where HBr is converted to bromine, which reacts with the benzene to produce bromobenzene. A catalyst may be employed to promote the reaction, such as an aluminum or iron-based catalyst, which could be incorporated into the anode structure, especially if it is a high surface area carbon-based material. More preferred, is to generate the bromine in the second region 118 from gaseous HBr, aqueous HBr, or NaBr, and then react the benzene as a liquid or as a gas with the bromine in a reactor containing, for example, an aluminum bromide or iron bromide catalyst on a carbon or inorganic support.

The bromobenzene may then be converted to phenols by a reaction with a sodium hydroxide solution, similar to the hydrolysis of chlorobenzene, with NaOH under pressure. In addition, bromobenzene may be reacted with nitric acid to form p-nitro-bromobenzene, which can then be converted after several other chemical processing steps to p-methoxyphenol. Other chemicals may be produced using bromobenzene as a raw starting material.

Many of the other reactions between bromine and the organics listed in Table 1 may also require catalysts or a radical initiator to achieve a desired bromination rate. These catalysts may be located in the anode structure, or in the second region 118 where the bromine and organic are reacted to form a brominated intermediate compound. For example, a catalyst may be a soluble catalyst dissolved in a solution phase within second region 118.

In addition, ultraviolet (UV) light has been shown to be an activator for the bromination reactions, where bromine forms a radical, and forms a chain reaction in brominating the organics. Designs in applying UV light into the electrochemical cell 102 itself using quartz glass light guides is possible, in addition to using glass piping in the product outlet lines and in the chemical reactors where the bromine and organic are reacted. Different wavelength light can be used to moderate the reactions for better control, as well as the use of light emitting diodes (LEDs) or lasers of differing light wavelengths are possible.

Referring to FIGS. 3A, 3B, 4A and 4B, block diagrams of systems 300, 400 in accordance with additional embodiments of the present disclosure are shown. Systems 300, 400 provide additional embodiments to systems 100, 200 of FIGS. 1-2 to co-produce a first product and second product.

Figure 3A:
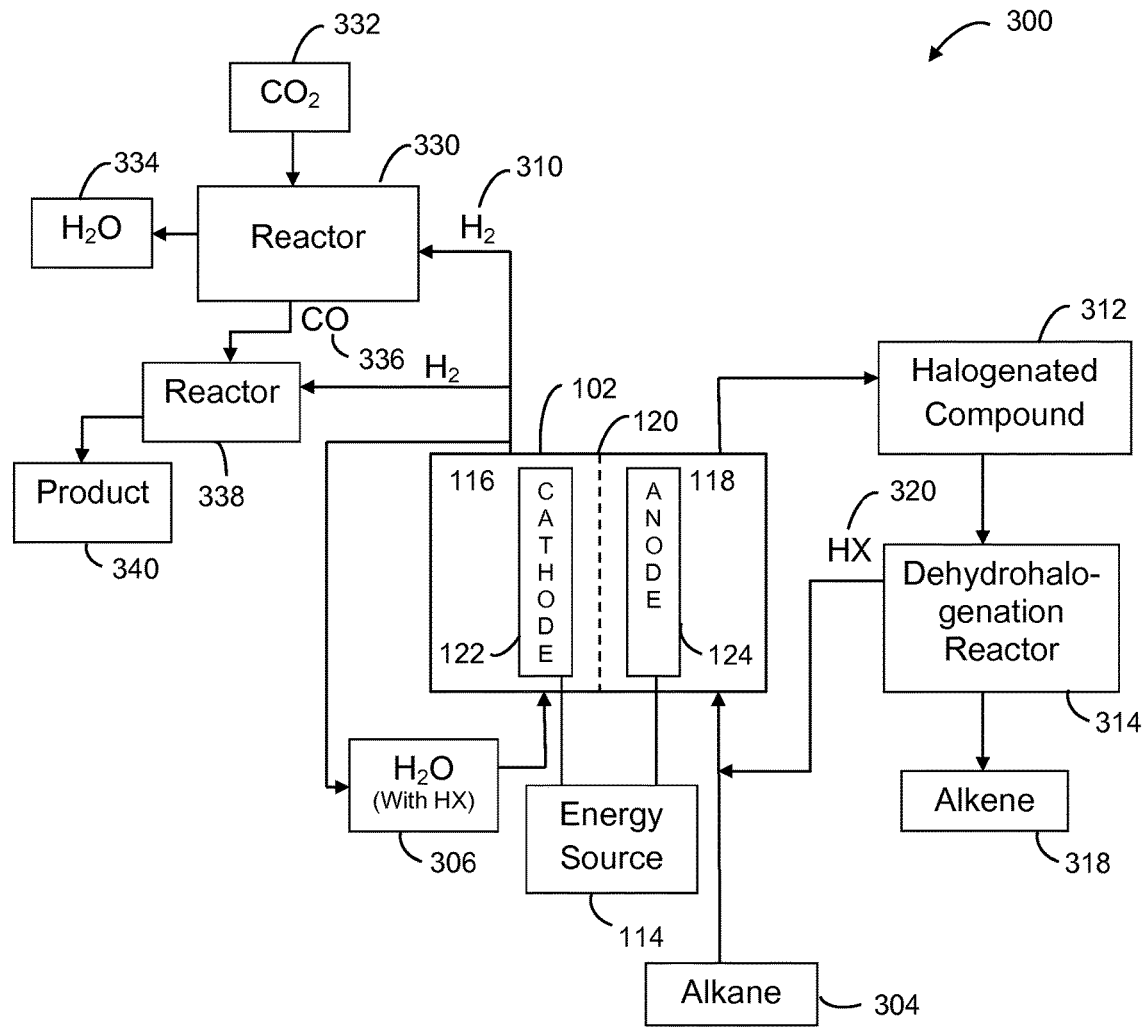
FIG. 3A is a block diagram of a system in accordance with an additional embodiment of the present disclosure.

Referring specifically to FIG. 3A, first region 116 of electrochemical cell 102 may produce a first product of $H_2$ 310 which is combined with carbon dioxide 332 in a reactor 330 which may perform a reverse water gas shift reaction. This reverse water gas shift reaction performed by reactor 330 may produce water 334 and carbon monoxide 336. Carbon monoxide 336 along with $H_2$ 310 may be combined at reactor 338. Reactor 338 may cause a reaction by utilizing $H_2$ 310 from the first region 116 of the electrochemical cell 102, such as a Fischer-Tropsch-type reaction, to reduce carbon monoxide to a product 340. Product 340 may include methane, methanol, hydrocarbons, glycols, olefins. Water 306, which may include a hydrogen halide, may be an additional product produced by the first region 116 and may be recycled as an input feed to the first region 116. Reactor 338 may also include transition metals such as iron, cobalt, and ruthenium as well as other transition metal oxides as catalysts, on inorganic support structures that may promote the reaction of CO with hydrogen at lower temperatures and pressures.

Figure 3B:
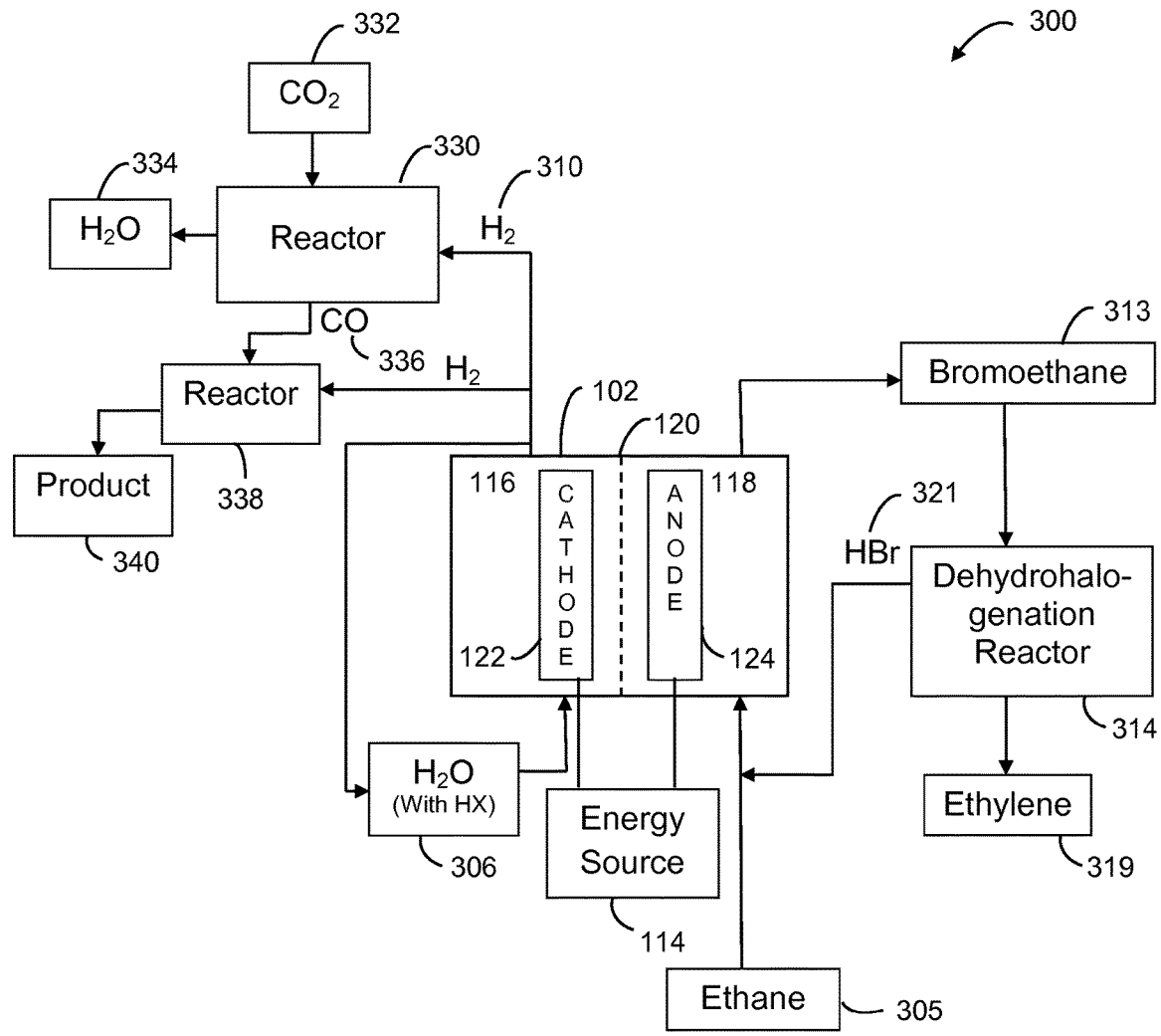
FIG. 3B is a block diagram of a system in accordance with an additional embodiment of the present disclosure.

Second region 118 may co-produce a halogenated compound 312, such as bromoethane, from a carbon-based reactant, such as an alkane 304 and a hydrogen halide recycled reactant 320, such as HBr. Halogenated compound 312 may be isolated, or may be supplied to a dehydrohalogenation reactor 314 to generate byproducts such as an alkene 318, for example, ethylene and a hydrogen halide recycled reactant 320, such as HBr, which is recycled back as an input feed to the second region 118. It is contemplated that alkane 304 may be other types of carbon-based reactants, including various types of alkanes, alkenes or aromatic compounds while halogenated compound 312 may also refer to any type of halogenated compound that may be supplied to a dehydrohalogenation reactor 314 to produce various types of alkenes, alcohols, glycols or olefins without departing from the scope or intent of the present disclosure. Referring to FIG. 3B, it is contemplated that second region 118 may co-produce a bromoethane 313, from a carbon-based reactant, such as an ethane 305. Bromoethane 313 may be isolated, or may be supplied to a dehydrohalogenation reactor 314 to generate products such as ethylene 319 and HBr 321 which is recycled back as an input feed to the second region 118.

Figure 4A:
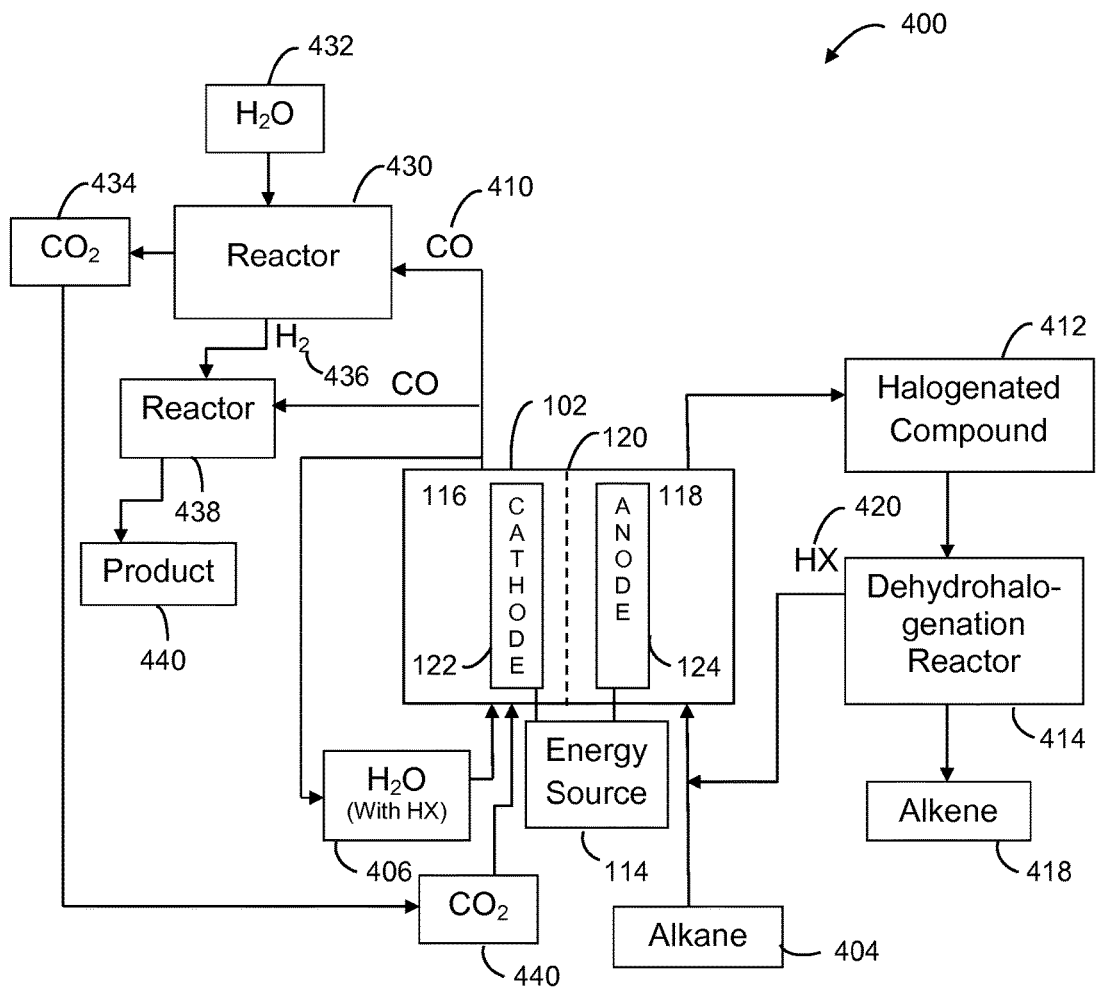
FIG. 4A is a block diagram of a system in accordance with an additional embodiment of the present disclosure.

Referring to FIG. 4A, first region 116 of electrochemical cell 102 may produce a first product of carbon monoxide 410 which is combined with water 432 in a reactor 430 which may perform a water gas shift reaction. This water gas shift reaction performed by reactor 430 may produce carbon dioxide 434 and $H_2$ 436. Carbon monoxide 410 and $H_2$ 436 may be combined at reactor 438. Reactor 438 may cause a reaction, such as a Fischer-Tropsch-type reaction, to reduce carbon monoxide to a product 440. Product 440 may include methane, methanol, hydrocarbons, glycols, olefins by utilizing $H_2$ 436 from the water gas shift reaction. Carbon dioxide 434 may be a byproduct of water gas shift reaction of reactor 430 and may be recycled as an input feed to the first region 116. Water 406, which may include a hydrogen halide, may be an additional product produced by the first region 116 and may be recycled as another input feed to the first region 116. Reactor 438 may also include transition metals such as iron and copper as well as other transition metal oxides as catalysts, on inorganic support structures that may promote the reaction of CO with hydrogen at lower temperatures and pressures.

Second region 118 of electrochemical cell 102 may co-produce a halogenated compound 412, such as bromoethane, from a carbon-based reactant such as an alkane 404 and a hydrogen halide recycled reactant 420, such as HBr. Halogenated compound 412, may be isolated, or may be supplied to a dehydrohalogenation reactor 414 to generate an alkene 418, such as ethylene and a hydrogen halide recycled reactant 420, such as HBr, which is recycled back as an input feed to the second region 118. It is contemplated that carbon-based reactant, such as an alkane 404, may be any type of alkane, alkene or aromatic compound while halogenated compound may also refer to any type of halogenated compound that may be supplied to a dehydrohalogenation reactor 414 to produce various types of alcohols, glycols or olefins without departing from the scope or intent of the present disclosure.

Figure 4B:
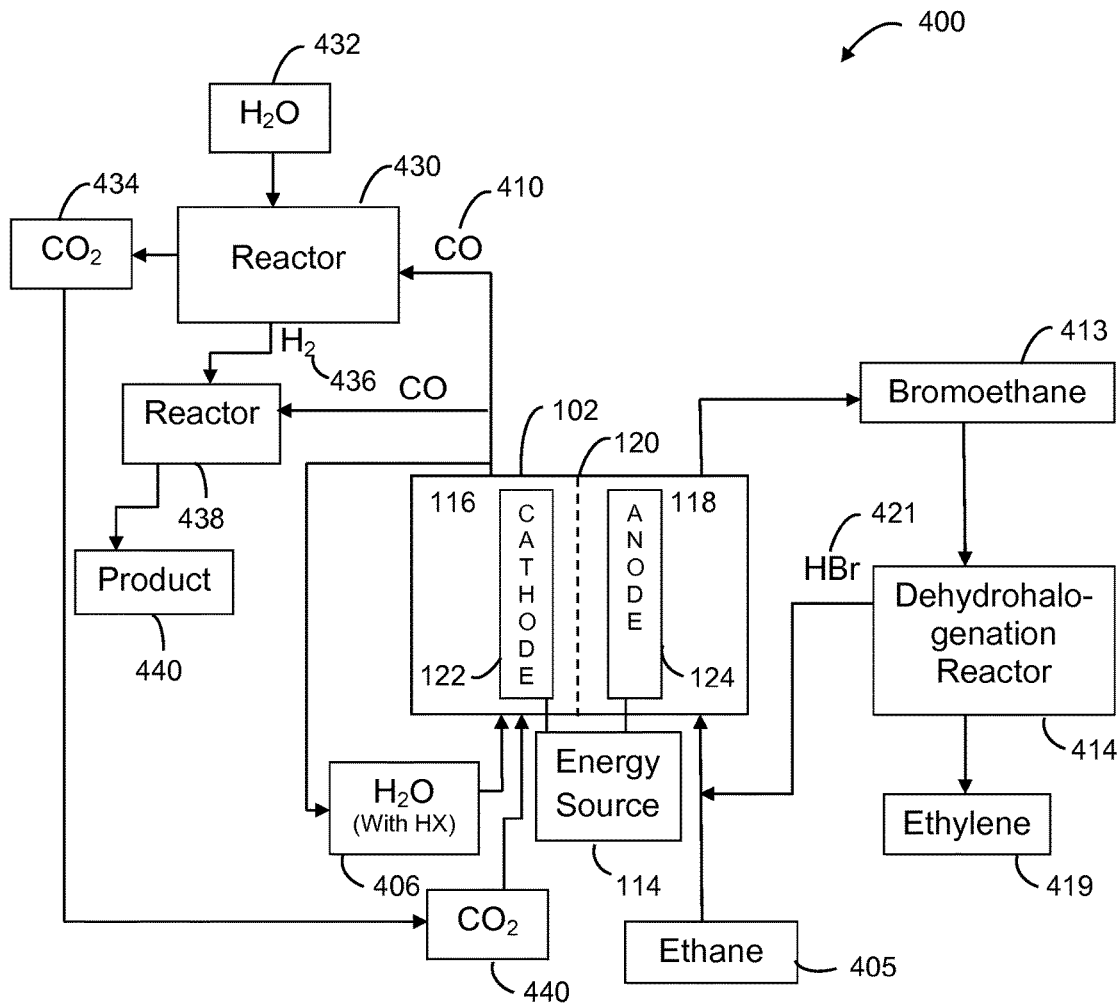
FIG. 4B is a block diagram of a system in accordance with an additional embodiment of the present disclosure.

Referring to FIG. 4B, it is contemplated that second region 118 may co-produce a bromoethane 413, from a carbon-based reactant, such as an ethane 405. Bromoethane 413 may be isolated, or may be supplied to a dehydrohalogenation reactor 414 to generate products such as ethylene 419 and HBr 421 which is recycled back as an input feed to the second region 118.

Figure 5:
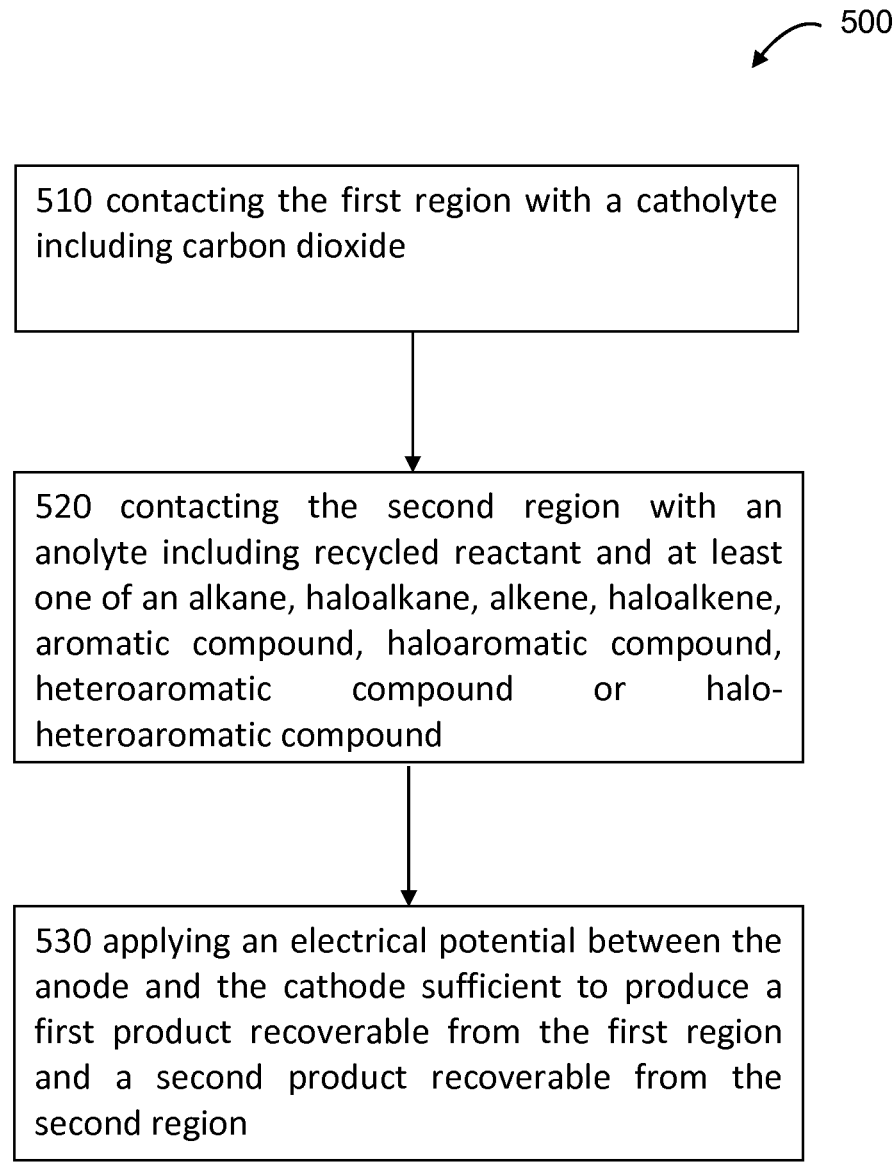
FIG. 5 is a flow diagram of a method of electrochemical co-production of products in accordance with an embodiment of the present disclosure.

Referring to FIG. 5 a flow diagram of a method 500 of electrochemical co-production of products in accordance with an embodiment of the present disclosure is shown. It is contemplated that method 500 may be performed by system 100 and system 200 as shown in FIGS. 1-2. Method 500 may include producing a first product from a first region of an electrochemical cell having a cathode and a second product from a second region of the electrochemical cell having an anode.

Method 500 of electrochemical co-production of products may include a step of contacting a first region of an electrochemical cell with a catholyte including carbon dioxide 510. Next, method 500 may include contacting a second region of an electrochemical cell with an anolyte including a recycled reactant and at least one of an alkane, haloalkane, alkene, haloalkene, aromatic compound, haloaromatic compound, heteroaromatic compound or halo-heteroaromatic compound 520. Method 500 may further include applying an electrical potential between the anode and the cathode sufficient to produce a first product recoverable from the first region and a second product recoverable from the second region 530. Advantageously, a first product produced at the first region may be recoverable from the first region and a second product produced at the second region may be recoverable from the second region.

Figure 6:
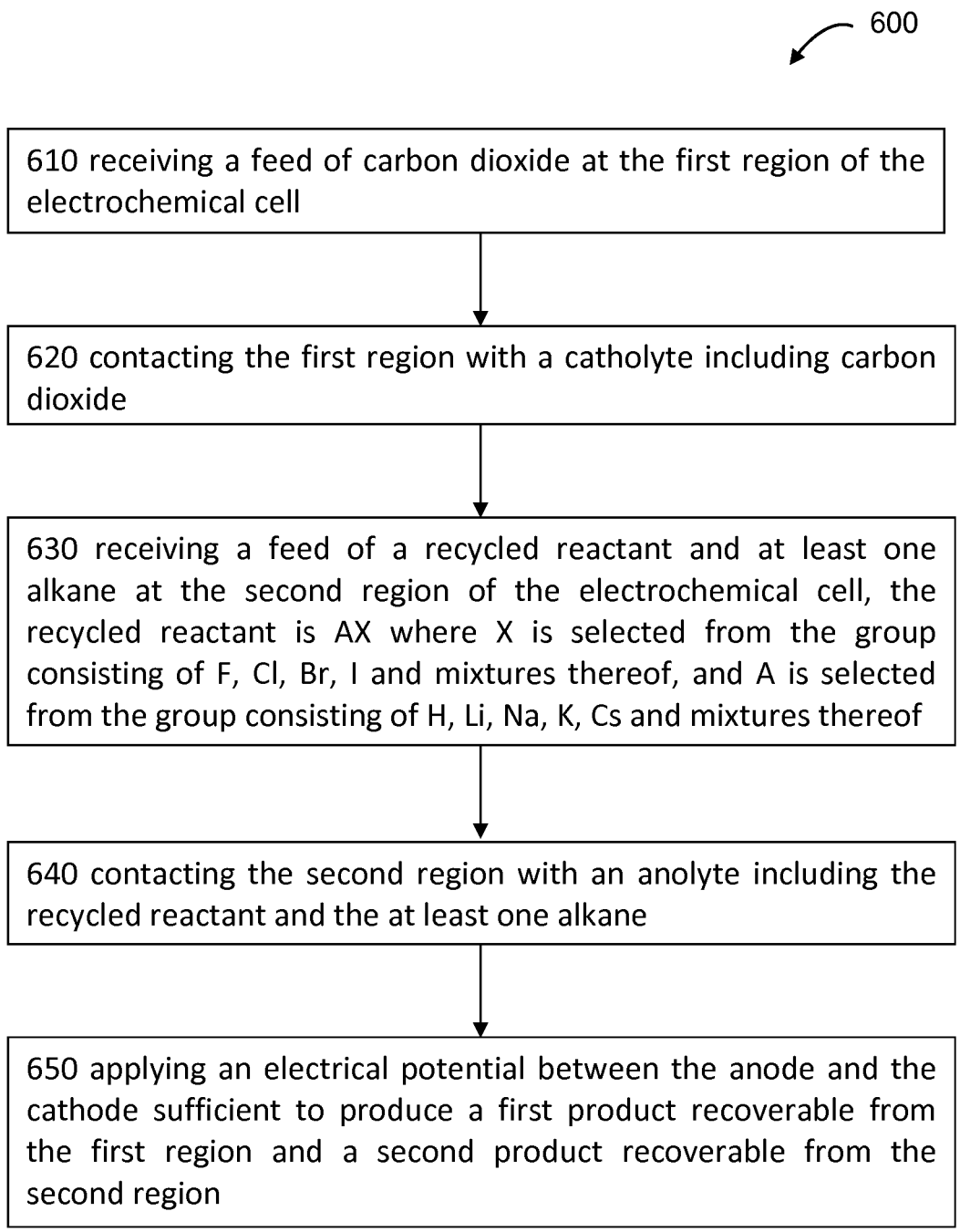
FIG. 6 is a flow diagram of a method of electrochemical co-production of products in accordance with another embodiment of the present disclosure.

Referring to FIG. 6, a flow diagram of a method 600 of electrochemical co-production of products in accordance with another embodiment of the present disclosure is shown. It is contemplated that method 600 may be performed by system 100 and system 200 as shown in FIGS. 1-2. Method 600 may include steps for producing a first product from a first region of an electrochemical cell having a cathode and a second product from a second region of the electrochemical cell having an anode.

Method 600 may include a step of receiving a feed of carbon dioxide at the first region of the electrochemical cell 610. Method 600 may further include contacting the first region with a catholyte comprising carbon dioxide 620. Next, method 600 may include receiving a feed of a recycled reactant and at least one alkane at the second region of the electrochemical cell, the recycled reactant is AX where X is selected from the group consisting of F, Cl, Br, I and mixtures thereof, and A is selected from the group consisting of H, Li, Na, K, Cs and mixtures thereof 630. Method 600 may further include contacting the second region with an anolyte comprising the recycled reactant and the at least one alkane 640. Method 600 may further include applying an electrical potential between the anode and the cathode sufficient to produce a first product recoverable from the first region and a second product recoverable from the second region 650.

It is contemplated that a receiving feed may include various mechanisms for receiving a supply of a product, whether in a continuous, near continuous or batch portions.

It is further contemplated that the structure and operation of the electrochemical cell 102 may be adjusted to provide desired results. For example, the electrochemical cell 102 may operate at higher pressures, such as pressure above atmospheric pressure which may increase current efficiency and allow operation of the electrochemical cell at higher current densities.

Additionally, the cathode 122 and anode 124 may include a high surface area electrode structure with a void volume which may range from 30% to 98%. The electrode void volume percentage may refer to the percentage of empty space that the electrode is not occupying in the total volume space of the electrode. The advantage in using a high void volume electrode is that the structure has a lower pressure drop for liquid flow through the structure. The specific surface area of the electrode base structure may be from 2 $cm^2/cm^3$ to 500 $cm^2/cm^3$ or higher. The electrode specific surface area is a ratio of the base electrode structure surface area divided by the total physical volume of the entire electrode. It is contemplated that surface areas also may be defined as a total area of the electrode base substrate in comparison to the projected geometric area of the current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

Cathode 122 may be selected from a number of high surface area materials to include copper, stainless steels, transition metals and their alloys and oxides, carbon, and silicon, which may be further coated with a layer of material which may be a conductive metal or semiconductor. The base structure of cathode 122 may be in the form of fibrous, reticulated, or sintered powder materials made from metals, carbon, or other conductive materials including polymers. The materials may be a very thin plastic screen incorporated against the cathode side of the membrane to prevent the membrane 120 from directly touching the high surface area cathode structure. The high surface area cathode structure may be mechanically pressed against a cathode current distributor backplate, which may be composed of material that has the same surface composition as the high surface area cathode.

In addition, cathode 122 may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni-Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si:B, degenerately doped n-Si, degenerately doped n-Si:As, and degenerately doped n-Si:B. These metals and their alloys may also be used as catalytic coatings on the various metal substrates. Other conductive electrodes may be implemented to meet the criteria of a particular application. For photoelectrochemical reductions, cathode 122 may be a p-type semiconductor electrode, such as p-GaAs, p-GaP, p-InN, p-InP, p-CdTe, p-GaInP$_2$ and p-Si, or an n-type semiconductor, such as n-GaAs, n-GaP, n-InN, n-InP, n-CdTe, n-GaInP$_2$ and n-Si. Other semiconductor electrodes may be implemented to meet the criteria of a particular application including, but not limited to, CoS, MoS$_2$, TiB, WS$_2$, SnS, Ag$_2$S, CoP$_2$, Fe$_3$P, Mn$_3$P$_2$, MoP, Ni$_2$Si, MoSi$_2$, WSi2, CoSi$_2$, Ti$_4$O$_7$, SnO$_2$, GaAs, GaSb, Ge, and CdSe.

Catholyte may include a pH range from 1 to 12, preferably from pH 4 to pH 10. The selected operating pH may be a function of any catalysts utilized in operation of the electrochemical cell 102. Preferably, catholyte and catalysts may be selected to prevent corrosion at the electrochemical cell 102. Catholyte may include homogeneous catalysts. Homogeneous catalysts are defined as aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., C1-C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxy-pyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

The catholyte may include an electrolyte. Catholyte electrolytes may include alkali metal bicarbonates, carbonates, sulfates, phosphates, borates, and hydroxides. The electrolyte may comprise one or more of Na$_2$SO$_4$, KCl, NaNO$_3$, NaCl, NaF, NaClO$_4$, KClO$_4$, K$_2$SiO$_3$, CaCl$_2$, a guanidinium cation, an H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide. In one embodiment, bromide salts such as NaBr or KBr may be preferred.

The catholyte may further include an aqueous or non-aqueous solvent. An aqueous solvent may include greater than 5% water. A non-aqueous solvent may include as much as 5% water. A solvent may contain one or more of water, a protic solvent, or an aprotic polar solvent. Representative solvents include methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, ionic liquids, and mixtures thereof.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells can operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator 120 or membrane separating the two regions. Special electrochemical designs may be employed to operate electrochemical units at higher operating pressures up to about 60 to 100 atmospheres or greater, which is in the liquid $CO_2$ and supercritical $CO_2$ operating range.

In another embodiment, a portion of a catholyte recycle stream may be separately pressurized using a flow restriction with backpressure or using a pump, with $CO_2$ injection, such that the pressurized stream is then injected into the catholyte region of the electrochemical cell which may increase the amount of dissolved $CO_2$ in the aqueous solution to improve the conversion yield. In addition, micro-bubble generation of carbon dioxide can be conducted by various means in the catholyte recycle stream to maximize carbon dioxide solubility in the solution.

Catholyte may be operated at a temperature range of −10 to 95° C., more preferably 5-60° C. The lower temperature will be limited by the catholytes used and their freezing points. In general, the lower the temperature, the higher the solubility of $CO_2$ in an aqueous solution phase of the catholyte, which would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing a portion, or all, of the catholyte through the heat exchanger and using cooling water to remove the heat and control the catholyte temperature.

Anolyte operating temperatures may be in the same ranges as the ranges for the catholyte, and may be in a range of 0° C. to 95° C. In addition, the anolyte may require cooling, so an external heat exchanger may be employed, flowing a portion, or all, of the anolyte through the heat exchanger and using cooling water to remove the heat and control the anolyte temperature.

Electrochemical cells may include various types of designs. These designs may include zero gap designs with a finite or zero gap between the electrodes and membrane, flow-by and flow-through designs with a recirculating catholyte electrolyte utilizing various high surface area cathode materials. The electrochemical cell may include flooded co-current and counter-current packed and trickle bed designs with the various high surface area cathode materials. Also, bipolar stack cell designs and high pressure cell designs may also be employed for the electrochemical cells.

Anode electrodes may be the same as cathode electrodes or different. Anode 124 may include electrocatalytic coatings applied to the surfaces of the base anode structure. Anolytes may be the same as catholytes or different. Anolyte electrolytes may be the same as catholyte electrolytes or different. Anolyte may comprise solvent. Anolyte solvent may be the same as catholyte solvent or different. For example, for HBr, acid anolytes, and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. For other anolytes, comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar electrochemical cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as metal halide or metal oxide catalysts such as iron halides, zinc halides, aluminum halides, cobalt halides, for the reactions between the bromine and the carbon-based reactant. For other anolytes comprising alkaline, or hydroxide electrolytes, anodes may include carbon, cobalt oxides, stainless steels, and their alloys and combinations.

Separator 120, also referred to as a membrane, between a first region 118 and second region 118, may include cation ion exchange type membranes. Cation ion exchange membranes which have a high rejection efficiency to anions may be preferred. Examples of such cation ion exchange membranes may include perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have a higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials can also be used if the anion rejection is not as desirable, such as those sold by Sybron under their trade name Ionac®, AGC Engineering (Asahi Glass) under their Selemion® trade name, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_1+xZr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte and operates at temperatures of less than 600 degrees C., and more preferably less than 500 degrees C.

A rate of the generation of reactant formed in the anolyte compartment from the anode reaction, such as the oxidation of HBr to bromine, is contemplated to be proportional to the applied current to the electrochemical cell 102. The rate of the input or feed of the carbon-based reactant, for example ethane, into the anolyte region 118 should then be fed in proportion to the generated reactant. The molar ratio of the carbon-based reactant to the generated anode reactant, such as $Br_2$, may be in the range of 100:1 to 1:10, and more preferably in the range of 50:1 to 1:5. The anolyte product output in this range can be such that the output stream contains little or no free bromine in the product output to the second product extractor 112, or it may contain unreacted bromine. The operation of the extractor 112 and its selected separation method, for example fractional distillation, the actual products produced, and the selectivity of the wanted reaction would determine the optimum molar ratio of the carbon-based reactant to the generated reactant in the anode compartment. Any of the unreacted components would be recycled to the second region 118.

Similarly, a rate of the generation of the formed electrochemical carbon dioxide reduction product 210, such as CO, is contemplated to be proportional to the applied current to the electrochemical cell 102. The rate of the input or feed of the carbon dioxide source 106 into the first region 116 should be fed in a proportion to the applied current. The cathode reaction efficiency would determine the maximum theoretical formation in moles of the carbon dioxide reduction product 210. It is contemplated that the ratio of carbon dioxide feed to the theoretical moles of potentially formed carbon dioxide reduction product would be in a range of 100:1 to 2:1, and preferably in the range of 50:1 to 5:1, where the carbon dioxide is in excess of the theoretical required for the cathode reaction. The carbon dioxide excess would then be separated in the extractor 110 and recycled back to the first region 116.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A system for electrochemical co-production of products, comprising:
 an electrochemical cell including:
  a first region;
  a cathode associated with the first region;
  a second region;
  an anode associated with the second region; and a separator for selectively controlling a flow of ions between the first region and the second region;

a carbon dioxide source, the carbon dioxide source in flow communication with the first region to supply carbon dioxide to the first region;

a carbon-based reactant source, the carbon-based reactant source in flow communication with the second region to supply a carbon-based reactant to said second region;

a recycled reactant source, the recycled reactant source in flow communication with the second region to supply a recycled reactant to the second region, the recycled reactant is AX where X is selected from the group consisting of F, Cl, Br, I and mixtures thereof, and A is selected from the group consisting of H, Li, Na, K, Cs and mixtures thereof; and an energy source for applying a current across the anode and the cathode, wherein when current is applied, a first product recoverable from the first region and a second product is recoverable from the second region.

2. The system according to claim 1, wherein the carbon-based reactant includes at least one of an alkane, haloalkane, alkene, haloalkene, aromatic compound, haloaromatic compound, heteroaromatic compound or halo-heteroaromatic compound.

3. The system according to claim 1, wherein the first product recoverable from the first region includes a carbon dioxide reduction product.

4. The system according to claim 1, wherein the second product recoverable from the second region includes a halogenated compound.

5. The system according to claim 1, wherein the separator selectively controls a flow of ions between the first region and the second region at a temperature less than 600 degrees C.

6. The system according to claim 1, wherein the separator includes an ion permeable barrier.

7. The system according to claim 6, wherein the ion permeable barrier includes at least one of a solid polymer conductor electrolyte material and a perfluorinated sulfonic acid based membrane, a sodium super-conducting ionic conductor type ceramics.

* * * * *